United States Patent [19]

Matthes et al.

[11] Patent Number: 5,053,560

[45] Date of Patent: * Oct. 1, 1991

[54] METHOD FOR THE CONTINUOUS PRODUCTION OF POTASSIUM TERT-BUTOXIDE

[75] Inventors: Rheinhard Matthes; Hartwig Rauleder, both of Rheinfelden; Hans-Joachim Vahlensieck, Wehr, all of Fed. Rep. of Germany

[73] Assignee: Huels Aktiengesellschaft, Troisdorf, Fed. Rep. of Germany

[ * ] Notice: The portion of the term of this patent subsequent to Mar. 18, 2003 has been disclaimed.

[21] Appl. No.: 363,292

[22] Filed: Jun. 7, 1989

Related U.S. Application Data

[63] Continuation of Ser. No. 139,775, Dec. 30, 1987, abandoned.

[30] Foreign Application Priority Data

Jan. 17, 1987 [DE] Fed. Rep. of Germany ..... 37012681

[51] Int. Cl.$^5$ ..................... C07C 29/70; C07C 31/12
[52] U.S. Cl. .................................................... 568/851
[58] Field of Search ........................................ 568/851

[56] References Cited

U.S. PATENT DOCUMENTS

| | | | |
|---|---|---|---|
| 1,712,830 | 5/1929 | Kyrides | 568/851 |
| 3,920,713 | 11/1975 | Feichtinger et al. | 568/851 |
| 4,150,244 | 4/1979 | Knorre et al. | 568/851 |
| 4,577,045 | 3/1986 | Matthes et al. | 568/851 |

FOREIGN PATENT DOCUMENTS 3413212 9/1985 Fed. Rep. of Germany ...... 568/851

*Primary Examiner*—J. E. Evans
*Attorney, Agent, or Firm*—Felfe & Lynch

[57] ABSTRACT

A method for the continuous production of anhydrous potassium tert-butoxide in a packed distillation column, wherein aqueous potash lye is fed with excess tert-butyl alcohol to the top of the column. Water formed in the reaction as well as water brought in with the reactants is distilled out at the top using methylcyclohexane or n-heptane as withdrawing agent. The amount of the withdrawing agent and of the tert-butanol must be selected such that above the column boiler a content between 0.2 and 2 wt.-% of the withdrawing agent is present in the gas mixture, while the gas mixture in the middle of the column has either between 32 and 34 wt.-% of methylcyclohexane or 36 to 38 wt.-% of n-heptane. The water together with the withdrawing agent and tert-butanol is withdrawn from the top of the column and then condensed. The organic phase of the condensate is fed back to the column.

2 Claims, No Drawings

METHOD FOR THE CONTINUOUS PRODUCTION OF POTASSIUM TERT-BUTOXIDE

This application is a continuation of application Ser. No. 139,775, filed Dec. 30, 1987, now abandoned.

BACKGROUND OF THE INVENTION

The subject matter of the present invention is a method for the continuous production of potassium tert-butoxide by the reaction of aqueous potash lye with excess tertiary butanol in a column in the presence of a withdrawing agent. In this method the potash lye and the tert-butanol are put into the top of the column and the water that forms in the reaction, as well as the water introduced by the reactants, is distilled out through the top by means of the withdrawing agent. In the boiler a solution of the potassium tert-butoxide in tert-butanol is formed; this solution is continuously withdrawn and the anhydrous salt is obtained from this withdrawn solution.

In the method described in U.S. Pat. No. 45 77 045 for the preparation of potassium tert-butoxide, the withdrawing agent used is cyclohexane or n-hexane. Furthermore, the amount of the withdrawing agent is selected such that at least half of the gas mixture present in the middle of the column is tert-butanol. In operating according to this method a potassium tert-butoxide is obtained which is anhydrous and has a maximum content of 0.8% KOH; however, the possible throughput of aqueous potash lye per unit of time is extremely low, so that the yield per unit of capacity and time is unsatisfactory in this process.

The problem therefore was to devise a continuous method for the production of anhydrous potassium tert-butoxide which would make it possible with the same expenditure of energy as in the method of U.S. Pat. No. 45 77 045 to increase the KOH throughput per unit time and at the same time obtain a product having at least the same qualities as the known products.

SUMMARY OF THE INVENTION

As the solution of this problem, a method has now been found for the continuous preparation of anhydrous potassium tert-butoxide, in which aqueous potash lye is reacted in a packed distillation column with excess tert-butyl alcohol by feeding these two reactants to the top of the column, distilling the water contained in the reaction mixture out of the top of the column with the aid of a withdrawing agent, adding the amount of organic phase withdrawn with the water back into the system and withdrawing the potassium tert-butoxide from the boiler of the column, which is kept at ebullition, in the form of a solution in tert-butanol. The claimed method is characterized by the fact that methylcyclohexane or n-heptane is used as the withdrawing agent, and that the gas mixture in the column directly above the boiler contains at the beginning of and during the addition of the aqueous potash lye and tert-butanol 0.5 to 2 wt.-% of the withdrawing agent, and in the middle of the column, when methylcyclohexane is used as withdrawing agent, between 32 and 34 wt.-% of the withdrawing agent, and when n-heptane is used as withdrawing agent, between 36 and 38 wt.-% of the withdrawing agent.

If these conditions are sustained the withdrawing agent is present within the said column during the reaction, while only 0.5 wt.-% of it is contained in the boiler. In the method of U.S. Pat. No. 45 77 045, on the other hand, the withdrawing agent is present only in a part of the column.

At the required percentage in the middle of the column, the withdrawing agents used according to the invention form with the tert-butanol an azeotropic mixture whose precise composition for the mixture of methylcyclohexane and tert-butanol is 34/66 wt.-%, and for the mixture of n-heptane and tert-butanol it is 38/62 wt.-%.

Above the boiler the gas mixture is to contain a minimum of withdrawing agent, not exceeding about 2 wt.-%. The rest of the gas mixture consists mostly of tert-butanol vapors. When the gas mixture above the boiler has the required content of withdrawing agents in the stated limits, the required content of withdrawing agents in the middle of the column can easily be adjusted.

The boiler of the column contains the potassium tert-butoxide dissolved in the excess tert-butanol. It is kept at the boiling temperature. Potassium tert-butoxide solution is continuously withdrawn from it, preferably through an overflow pipe, and anhydrous potassium tert-butoxide is isolated from it in a known manner, e.g., by removing the tert-butanol by vacuum distillation.

A gaseous mixture of withdrawing agent, tert-butanol and water vapor, whose content no longer corresponds to the above-described composition of the azeotrope, leaves the top of the column. This gas mixture exiting at the top is then condensed and, in a phase separating vessel, it is separated into the organic phase and water. The aqueous phase thus produced contains both the water contained in the starting products and the water that forms in the reaction. This phase can contain up to about 15% of dissolved tert-butanol.

The organic phase produced in the phase separation is best recycled to the distillation column, preferably to the top of the column or the upper part of the column. It contains mostly the withdrawing agent and the part of the distilled tert-butanol that is not dissolved in the water. However, other use can be made of the organic phase. In this case, however, care must be taken that the corresponding amount of withdrawing agent, which is contained in this organic phase, is fed to the column.

The aqueous potash lye used in the process is preferably a concentrated lye from which solid potassium hydroxide does not precipitate under the conditions of the reaction. Lyes with KOH contents between 50 and 60 wt.-% are quite usable. The KOH content can also be lower, but then corresponding amounts of water must be distilled out. For this reason the use of potash with KOH contents under 38 wt.-% is not recommendable.

In the procedure according to the invention the tert-butanol does not need to be absolutely anhydrous. Moisture contents under 11.76 wt.-% (composition of the tert-butanol/water azeotrope) have virtually no adverse effect on the procedure according to the invention. Preferably, however, the tert-butanol is to have a water content under 0.1 wt.-%.

The tert-butanol is used in the amount that is necessary for the formation of the potassium tert-butoxide, plus the amount that is continuously withdrawn from the boiler as solvent for this product. In the case in which the organic phase separated through the top is not fed back to the column, the input tert-butanol must also contain the amount that is continuously lost through the top.

Packings known in the distillation art are used for packing the column. Preferably noble metal mesh packing is used.

In a variant of the present method according to the invention, a portion of the claimed withdrawing agent is replaced by cyclohexane in the top part of the column. This portion can be no more than will be sufficient to enable the gas phase leaving through the top to contain so much cyclohexane that, after condensation and phase separation, the organic phase will have a content of up to 20 wt.-% of cyclohexane.

The procedure according to the invention makes it possible, with the same energy consumption as in the known process, to put through up to one-third more KOH per unit time and obtain products of the same quality as in the known process.

The method of the invention is best practiced in a high-grade steel distillation column which is packed with a high-grade steel mesh packing, and to which a phase separating vessel is attached for the separation of the aqueous from the organic phase and returning the organic phase to the top of the column. The distillation vessel at the bottom of the column is provided with an overflow for the removal of the solution of potassium tert-butoxide in tert-butanol that is produced. The cross section of the column is preferably 400 mm, the effective height preferably 10 meters.

To set up the column, an amount of water sufficient for the phase separation is placed in the phase separation vessel and tert-butanol is heated to ebullition in the boiler. The withdrawing agent and the cyclohexane, if used, are then added in such amounts that the conditions described below establish themselves. The methylcyclohexane or n-heptane and cyclohexane amounts are selected such that the composition of the condensate in the middle of the column corresponds to the composition of the tert-butanol/methylcyclohexane or tert-butanol/n-heptane azeotrope. Before and during the addition of potash lye and tert-butanol the methylcyclohexane or n-heptane is to be still detectable at 0.5 to 2 wt.-% in the gas chamber above the boiler, and in the organic phase recycled to the column the cyclohexane content is to amount preferably to 14 to 17 wt.-%. Once this composition is established it is to be sustained throughout the reaction.

In a column thus prepared, concentrated aqueous potash lye and tert-butanol are then fed in continuously. The solution water and reaction water that separate are continuously withdrawn from the phase separating vessel and the solution of potassium tert-butoxide in tert-butanol is continuously withdrawn from the boiler maintained at ebullition, the alcohol-free potassium tert-butoxide being obtained therefrom in a known maner. The method according to the invention permits a throughput of KOH per unit time that can be up to one-third greater than in the prior-art methods, at the same energy consumption and with the same product quality.

EXAMPLE 1

The process is performed in a column as described above. Tert-butanol is put into the boiler of the column and boiled with refluxing. Then n-heptane is added in such an amount that it is detectable in the middle of the column. Then follows the addition of cyclohexane in such an amount that it it becomes detectable at 15 wt.-% in the organic phase recycled to the column. Then more n-heptane is added until it can be detected at 1 wt.-% in the gas mixture immediately above the boiler (at the beginning of the first column shot over the boiler).

With an hourly feed of 2.52 kg of 50% KOH and 17 kg of tert-butanol, a 14% solution of potassium tert-butoxide in tert-butanol is obtained. This solution yields a product with a KOH content of 0.76%.

EXAMPLE 2

The procedure is similar to Example 1, with a methylcyclohexane-methylcyclohexane/cyclohexane withdrawing agent. The 50% aqueous KOH is fed in at a rate of 2.53 kg per hour, and tert-butanol at a rate of 17 kg per hour.

A product containing 0.73% KOH is obtained from the 14% solution of potassium tert-butoxide in tert-butanol.

We claim:

1. Method for the continuous production of anhydrous potassium tert-butoxide by the reaction of aqueous potassium hydroxide with excess tert-butanol in a packed distillation column to the top of which the aqueous potash lye and excess tert-butanol are fed, removal of the water by distillation using a withdrawing agent, continuous feeding into the upper part of the column of an organic phase identical to the organic phase which was obtained, after phase separation, from the mixture distilled out from the top, and withdrawal of the solution of the potassium tert-butoxide in tert-butanol produced in the boiler of the column, characterized in that
   a) methylcyclohexane or n-heptane is used as withdrawing agent,
   b) at the beginning and during the feeding of the aqueous potash lye and tert-butanol a gas mixture is established in the column, which contains 0.5 to 2 wt.-% of the withdrawing agent, and
   c) The content of withdrawing agent in the gas mixture at the middle of the column amounts to between 32 and 34 wt.-% when methylcyclohexane is the withdrawing agent and between 36 and 38 wt.-% when n-heptane is the withdrawing agent.

2. Method according to claim 1, characterized in that, before the feeding of the potash lye and the tert-butanol, tert-butanol is maintained at ebullition in the boiler of the column and then the withdrawing agents are fed in in the required amount.

* * * * *